United States Patent [19]

Bolasco

[11] 4,242,354
[45] Dec. 30, 1980

[54] 2-(2-THENOLYTHIO)-PROPIONYLGLY-CINE: METHOD FOR ITS PREPARATION AND PHARMACEUTICAL FORMULATIONS CONTAINING SAID COMPOUND

[75] Inventor: Franco Bolasco, Rome, Italy

[73] Assignee: Mediolanum Farmaceutici s.r.l. Milan, Italy

[21] Appl. No.: 26,933

[22] Filed: Apr. 4, 1979

[30] Foreign Application Priority Data

Apr. 11, 1978 [IT] Italy ............................. 22175 A/78
Feb. 12, 1979 [IT] Italy ............................. 20111 A/79

[51] Int. Cl.$^2$ ..................... A01N 9/00; C07D 333/24
[52] U.S. Cl. ................................. 424/275; 549/76
[58] Field of Search ............... 260/332.2 C, 455 R; 424/275; 549/76

[56]  References Cited

U.S. PATENT DOCUMENTS

| 2,510,773 | 6/1950 | Clinton | 260/455 R |
| 2,632,735 | 3/1953 | Hawley | 260/455 R |
| 2,669,564 | 2/1954 | Clinton | 260/455 R |

Primary Examiner—Alan Siegel
Attorney, Agent, or Firm—Bucknam and Archer

[57]  ABSTRACT

The invention provides 2-(2-thenoylthio)-propionylglycine, a novel compound having liver-protective, mucolytic and bronchial-spasm relieving activity.

5 Claims, No Drawings

2-(2-THENOLYTHIO)-PROPIONYLGLYCINE: METHOD FOR ITS PREPARATION AND PHARMACEUTICAL FORMULATIONS CONTAINING SAID COMPOUND

The present invention concerns a new compound, precisely 2-(2-thenoylthio)-propionylglycine, characterized by the following structural formula (I):

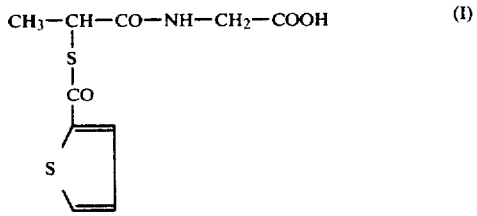

as well as its pharmaceutically acceptable salts.

The invention, moreover, also concerns processes for the preparation of the compound (I). Furthermore, the present invention concerns pharmaceutical formulations containing as the active ingredient the compound (I), or its pharmacologically acceptable salts, suited for the treatment of acute and chronic liver diseases as well as for poisoning consequences.

Finally pharmaceutical preparations, endowed with a mucolytic and bronchial-spasm relieving activity, containing as the active ingredient the compound or its pharmacologically acceptable salts, are also the object of the present invention.

It is known that 2-mercaptopropionylglycine (II)

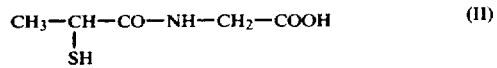

is endowed with an interesting pharmacological activity, that makes said compound suited for the treatment of acute and chronic liver diseases as well for poisoning consequences. Unfortunately, 2-mercaptopropionylglycine (II) shows various inconveniences due to its low stability. The most relevant of said inconveniences is represented by the unpleasant smell scented by the formulations of compound (II) even after a short-term storage: said characteristics exerts obviously negative psychological effects on the patient while impairing, concurrently, the therapeutic properties of the formulation. Said instability of 2-mercaptopropionylglycine (II) increases obviously with the increase of temperature, as may happen in warm climates or obviously in tropical countries.

It has now been observed that 2-(2-thenoylthio)-propionylglycyne, characterized by the above mentioned structural formula (I), is endowed with optimal pharmacological characteristics that make it definitely suitable for the treatment of acute and chronic liver diseases as well as poisoning consequences, being also endowed with a stability much higher than of compound (II). The complete absence of odor and taste, characteristic of the compound according to the invention, guarantees moreover its optimal clinical tolerability by the gastrointestinal tract under variously tested conditions.

It was also surprisingly discovered that 2-(2-thenoylthio)-propionylglycine is endowed with an interesting mucolytic and bronchial-spasm relieving activity that enable the use of said compound in the treatment of acute infections of the respiratory tract characterized by bronchial hypersecretion as well as in the treatment of mucoviscidosis syndromes and other similar affections.

According to the invention, the compound (I) results from the reaction of the chloride of thiophen-2-carboxylic acid with 2-thiopropionylglycine in the presence of a base. The reaction can be performed in an aqueous medium using, as the base, the carbonate of an alkaline metal, specifically sodium or potassium carbonate. The method, according to the invention, is illustrated, but not limited, by the following example.

EXAMPLE

Two-hundred and seventy-eight (278) grams of mercaptopropionylglycine are introduced into 1,600 ml water. The resulting suspension is added cautiously, while stirring, with 653 grams of potassium carbonate. Still under agitation, the resulting solution is added dropwise with 240 grams of thiophen-2-carboxylic acid chloride.

The temperature is kept at 20° C.

The resulting solution is shaken up to a complete disappearance of acylic chloride drops (4 hours approximately).

The solution is thereafter cautiously acidified up to a pH 3 with 10 percent sulfuric acid.

A crystalline precipitate is obtained that, just after, is collected by filtration, washed with distilled water, and dried in the air at 40° C. 472 grams of colorless product are thereafter obtained following an acetonitrile recrystallization, characterized by a melting point of 168°-170° C. The nature of the compound is confirmed by its related analytical and spectroscopic data (IR, NMR). The compound (I) is soluble in a saturated solution of NaHCO$_3$, and also in chloroform; it is scarcely soluble in all other inorganic solvents. The compound is odorless and practically tasteless.

As already said, 2-(2-thenoylthio)-propionylglycine has been showing a remarkable liver-protection activity that, as results from the below specified investigations, proves to be significantly higher than that exerted by 2-mercaptopropionylglycine that was used as reference drug. Also the toxicological data proved definitely satisfactory, as results from the below reported considerations.

TESTS OF TOXICITY (a) Acute Toxicity in the Mouse

Albino mice, Swiss strain, bodyweight 20–23 grams, subdivided into groups of 5 animals, kept on fast 16 hours before the investigation and given water freely, were used for the test. 2-(2-thenoylthio)-propionylglycine (I) and 2-mercaptopropionyl-glycine (II) were given both orally and intravenously, in a single administration, at progressively increasing doses given at regular intervals of time.

Oral LD 50

The oral LD 50 resulted to be higher that 2,500 mg/kg for both compounds. However, while no animal died even at the highest dose administered of 2-(2-thenoylthio)-propionylglycine, the reference drug induced an animal 20 percent mortality at the dose of 2,500 mg/kg (Table 1).

Intravenous LD 50

The intravenous LD 50 proved higher than 1,250 mg/kg for both compounds. Also in this case no deaths were encountered in the case of compound (I) while the reference drug induced a 30 percent mortality at the dose of 1,250 mg/kg (Table 2).

(b) Acute Toxicity in the Rat

Hundred-and-forty (140) albino rats, Sprague-Dawley strain, bodyweight 120–135 grams, subdivided into groups each consisting of 5 animals, were used for the investigation. The animals, kept on fast 16 hours before the treatment, were given, both orally and intramuscularly, in a single administration and in increasing doses, the two compounds, ie 2-(2-thenoylthio)-propionylglycine (I) and 2-thiopropionylglycine (II) (reference drug). For each single compound the LD 50 was assessed according to Litchfield and Wilcoxon on the basis of the mortality rate encountered in the 7 days following the treatment.

Oral LD 50

Also in the rat no deaths were encountered up to highest dose of compound (I) while, in the case of the reference drug, a 20 percent mortality rate was observed at the highest dose (Table 3).

Intramuscular LD 50

The LD 50 of the investigational product proved equivalent to 1801 mg/kg while it resulted to be 1630 mg/kg in the case of the reference drug (Table 4).

TABLE 1

Oral LD 50 in the mouse

| Compound given | Dose mg/kg | No. Animals per Dose | No. Animals Dead | % percent mortality | LD 50 |
|---|---|---|---|---|---|
| I | 1500 | 10 | 0 | 0 | |
|   | 2000 | 10 | 0 | 0 | 2500 |
|   | 2500 | 10 | 0 | 0 | |
| II | 1500 | 10 | 0 | 0 | |
|    | 2000 | 10 | 1 | 10 | 2500 |
|    | 2500 | 10 | 2 | 20 | |

TABLE 2

Intravenous LD 50 in the mouse

| Compound given | Dose mg/kg | No. Animals per Dose | No. Animals Dead | percent mortality | LD 50 |
|---|---|---|---|---|---|
| I | 500 | 10 | 0 | 0 | |
|   | 750 | 10 | 0 | 0 | |
|   | 1000 | 10 | 0 | 0 | 1250 |
|   | 1250 | 10 | 0 | 0 | |
| II | 500 | 10 | 0 | 0 | |
|    | 750 | 10 | 0 | 0 | |
|    | 1000 | 10 | 1 | 10 | 1250 |
|    | 1250 | 10 | 3 | 30 | |

TABLE 3

Oral LD 50 in the rat

| Compound given | Dose mg/kg | No. Animals per Dose | No. Animals Dead | percent mortality | LD 50 |
|---|---|---|---|---|---|
| I | 1500 | 10 | 0 | 0 | |
|   | 2000 | 10 | 0 | 0 | 2500 |
|   | 2500 | 10 | 0 | 0 | |
| II | 1500 | 10 | 0 | 0 | |
|    | 2000 | 10 | 0 | 0 | |
|    | 2500 | 10 | 2 | 20 | |

TABLE 4

Intramuscular LD 50 in the rat

| Compound given | Dose mg/kg | No. Animals per Dose | No. Animals Dead | percent mortality | LD 50 |
|---|---|---|---|---|---|
| I | 1250 | 10 | 0 | 0 | |
|   | 1500 | 10 | 1 | 0 | |
|   | 1750 | 10 | 4 | 40 | 1801 |
|   | 2000 | 10 | 10 | 100 | (1747–1864) |
| II | 1250 | 10 | 0 | 0 | |
|    | 1500 | 10 | 2 | 20 | 1630 |
|    | 1750 | 10 | 6 | 60 | |
|    | 2000 | 10 | 10 | 100 | (1580–1692) |

(c) Chronic Toxicity in the Rat and in the Dog

Rats: 80 albino rats (Sprague Dawley—100 grams bodyweight), subdivided into 2 groups: (1) control (carboxymethylcellulose; (2) 2-(2-thenoylthio)-propionylglycine (200 mg/kg/im) were used for the investigation.

The treatments were given daily, 6 times weekly for 16 weeks.

| Results: | mortality | in the norm |
|---|---|---|
| | general conditions | optimal |
| | tolerability | optimal |
| | behavior | normal in treated and control animals |
| | bodyweight gain | higher than in the controls |
| | blood morphology and chemistry parameters | as in the controls |
| | organs weight | as in the controls |

The results were optimal also in the dogs.

PROTECTIVE ACTIVITY IN THE CARBON TETRACHLORIDE POISONING

Fifty male rats (Sprague-Dawley, 180–200 grams bodyweight) were used for the investigation, subdivided into 5 groups: one group was given no treatment while the remaining 4 groups were poisoned for 7 consecutive days with $CCl_4$ at the dosage of 0.5 ml/mg given subcutaneously. The animals were concurrently given intramuscularly 2-(2-thenoylthio)-propionylglycine (200 and 300 mg/kg) and 2-thiopropionylglycine (300 mg/kg).

Results: both the investigational compound and 2-thiopropionyl-glycine can prevent the liver weight increase consequent to the administration of $CCl_4$.

Moreover, the two drugs exerted a favorable effect on the liver lipids (the fats content proves reduced) and proteins (the protein content proves markedly higher than that encountered in the animals given only poisoning treatment).

Upon equivalent dosage the compound (I) showed, in comparison with 2-mercaptopropionylglycine, a statistically significant efficacy in preventing the liver weight increase as well as in reducing the liver fats levels.

PROTECTIVE ACTIVITY IN THE BROMOBENZENE POISONING

Fifty male rats (Sprague-Dawley, 180–200 g body-weight) were used for the investigation, subdivided into 5 groups, each consisting of 10 animals, given orally the following compounds (1) 5 percent gum arabic in tap water
(2) 5 percent gum arabic in tap water
(3) 2-(2-thenoylthio)-propionylglycine—200 mg/kg
(4) 2-(2-thenoylthio)-propionylglycine—300 mg/kg
(5) 2-mercaptopropionylglycine (300 mg/kg).

Seven days later, the animals of the groups 2-3-4-6 were given bromobenzene subcutaneously (150 mg/rat) while the remaining group (control) was given an equivalent volume of saline. Still seven days later, 5 of the animals of each group were given Nembutal (25 mg/kg/intraperitoneally), and the sleeping time was calculated.

The remaining 5 animals of each group were given bromophthalein at the dose of 50 mg intravenously; thirty minutes later, the animals were sacrificed and both the present bromophthalein and SGPT (serum glutamic pyruvic transaminase) were established in the blood.

Results: the investigational drug proved able to reduce the liver impairment induced by bromobenzene with a consequent statistically significant decrease of the sleeping time. The treatment with the drug induced a significant reduction of the serum concentrations of SGPT, markedly increased by the liver impairment produced by bromobenzene.

The rate of excretion of bromophthalein resulted less evident, after administration of 2-(2-thenoylthio)-propionylglycine, than in the case of poisoned controls.

As results from the survey of said parameters, 2-thiopropionylglycine exerted a liver protective effect lower than that induced by the investigational compound, and statistically not significant.

"IN VIVO" PROTECTIVE ACTION AGAINST MERCURIAL COMPOUNDS

Forty male mice (Swiss strain, 22 grams mean body-weight) were used for the investigation, subdivided into 4 groups treated as follows:

(1) mercuric chloride, 20 mg/kg/intraperitoneally;
(2) mercuric chloride 20 mg/kg/intraperitoneally + compound (I) 200 mg/kg/intraperitoneally.
(3) mercuric chloride 20 mg/kg/intraperitoneally + compound (I) 300 mg/kg/intraperitoneally.
(4) mercuric chloride 20 mg/kg/intraperitoneally + 2-thiopropionylglycine 300 mg/kg/intraperitoneally.

Deaths occurred were recorded hourly in the first 5 hours, and thereafter after 24 hours.

Results: all the animals given the only mercuric chloride died in the 24 hours subsequent to the treatment.

| | |
|---|---|
| compound (I) 200 mg/kg/intraperitoneally | |
| 2-thiopropionylglycine 300 mg/kg intraperitoneally | 10 percent of deaths |
| compound (I), 300 mg/kg/intraperitoneally. | |

TESTS OF STABILITY

As already specified initially, 2-(2-thenoylthio)-propionylglycine (I) is markedly more stable than the correspondent 2-thiopropionylglycine (II).

The stability tests were carried out according to the Rogers' nonisothermic method suitably integrated by the evaluation of physical data, melting point, weight variation, and spectrophotometric assay. For each single compound, the tests were performed on a series of samples, with the weight of 100 milligrams, added for the wet tests with 1 ml of distilled water. In the case of compound (I) a white suspension was therefore obtained while 2-thiopropionylglycine produced a clear solution. Table 5 shows the results pertaining to the appearance, to the physical properties and to the weight variations. The sample were kept in a thermostat at increasing temperatures, i.e. from 25° to 80° C. The final temperature was chosen considering the lowest melting point of the two investigational compounds (2-thiopropionylglycine, melting point 93°–95° C.). The temperature, programmed according to the Rogers' formula, resulted to be 40° C. at the end of the first hour, 50° C. at the end of the second hour, 57° C. at the end of the third hour, 63° C. at the end of the fourth hour, 69° C. at the end of the fifth hour, 73° C. at the end of the sixth hour, 77° C. at the end of the seventh hour and, as already specified, 80° C. at the end of the eighth hour.

Still in Table 5, the sample from 1 to 5 refer, for each of the two compounds, to the dry substance while the samples from 6 to 10 refer to the solution or to the aqueous suspension obtained as above specified.

The final weight of the various samples was calculated at the time of the extraction from the thermostat, ie one hour and thirty minutes for the samples No. 1, 3 hours for the samples No. 2, 5 hours and 15 minutes for the samples No. 3, 8 hours for the samples No. 4 and No. 5. In the case of the wet-treated samples, the final weight was only established on the samples No. 10 brought to dryness at 60° C. under vacuum after an 8-hour heating.

TABLE 5

PHYSICAL PROPERTIES AND WEIGHT VARIATIONS

| Sub-stance | Sam-ple | Color | Smell | Weight (mg) Init. | Weight (mg) Fin. | Variations % |
|---|---|---|---|---|---|---|
| 2-thio-propionyl-glycine | 1 | white | mildly mercaptanic | 98.7 | 98.3 | −5.4 |
| | 2 | " | mildly mercaptanic | 99.0 | 93.0 | ∼6.06 |
| | 3 | " | mildly mercaptanic | 100.5 | 94.8 | −5.67 |
| | 4 | " | mildly mercaptanic | 101.3 | 95.7 | −5.53 |
| | 5 | " | markedly mercaptanic | 204.7 | 198.9 | −2.83 |
| | 6 | colorless | mildly mercaptanic | 101.6 | — | |
| | 7 | " | mildly mercaptanic | 102.1 | — | |
| | 8 | " | mildly mercaptanic | 100.4 | — | |
| | 9 | yellowish | mildly mercaptanic | 98.5 | — | |
| | 10 | anhydrous conditions: yellow powder | anhydrous conditions: markedly mercaptanic | 200.0 | 193.8 | −3.1 |
| 2-(2-the-noyl-thiopro-pionyl-glycine | 1 | white | almost absent | 100.7 | 95.4 | −5.26 |
| | 2 | " | " | 99.5 | 94.5 | −5.03 |
| | 3 | " | " | 100.5 | 95.1 | −5.37 |
| | 4 | " | " | 100.7 | 94.9 | −5.74 |
| | 5 | " | " | 201.5 | 194.1 | −3.67 |
| | 6 | white suspension white sus- | " | 100.4 | — | |

TABLE 5-continued

PHYSICAL PROPERTIES AND WEIGHT VARIATIONS

| Sub-stance | Sam-ple | Color | Smell | Weight (mg) Init. | Weight (mg) Fin. | Variations % |
|---|---|---|---|---|---|---|
| | 7 | white suspension | " | 103.2 | — | |
| | 8 | white suspension | " | 101.0 | — | |
| | 9 | white suspension | " | 95.6 | — | |
| | 10 | anhydrous conditions: white powder | anhydrous conditions: almost absent | 207.4 | 201.3 | −2.94 |

The melting point was established in a capillary tube, under identical conditions, on the samples No. 5 after heating for 8 hours in the previously specified conditions, and on the samples No. 10 after heating and evaporation to dryness as previously specified. Table 6 shows the results obtained; while the compound (I) shows no variations, 2-thiopropionyl-glycine (II) shows a marked decrease of the melting point in the case of the wet sample.

TABLE 6

MELTING POINT

| PRODUCT | Initial m.p. | Final m.p. dry conditions (Sample 5) | wet conditions (Sample 10) |
|---|---|---|---|
| II | 93–95° C. | 92–94° C. | 86–88° C. |
| I | 166–167° C. with decomposition | 166–167° C. with decomposition | 166–167° C. with decomposition |

Also the variations of the results of the spectrophotometric assays of the two compounds, upon varying times of heating, leads to formulate significant considerations.

It shall be considered that 2-thiopropionylglycine shows a maximal extinction E=0.329 at 232 nm while the compound (I) shows an E=0.438 at 292 nm.

The samples 1–9 of the two compounds, at the above stated times of heating, show the extinction (and of spectrophotometric assay) variations specified in Table 7: the better stability of the compound (I), according to the invention proves evident.

TABLE 7

EXTINCTIONS AND SPECTROPHOTOMETRIC ASSAY

| Substance | Sample no. | Weight mg | E at 232 nm | E at 292 nm | Content % |
|---|---|---|---|---|---|
| 2-thiopropionylglycine (II) | (as such) | 99.8 | 0.329 | — | 101.43 |
| | 1 | 98.7 | 0.325 | — | 101.32 |
| | 2 | 99.0 | 0.324 | — | 100.70 |
| | 3 | 100.5 | 0.325 | — | 99.50 |
| | 4 | 101.3 | 0.324 | — | 98.41 |
| | 6 | 101.6 | 0.333 | — | 100.85 |
| | 7 | 102.1 | 0.325 | — | 97.94 |
| | 8 | 100.4 | 0.320 | — | 98.06 |
| | 9 | 98.5 | 0.300 | — | 93.71 |
| 2-(2-thenoyl thio)-propionylglycine (I) | (as such) | 100.0 | — | 0.438 | 100.0 |
| | 1 | 100.7 | — | 0.440 | 99.76 |
| | 2 | 99.5 | — | 0.435 | 99.81 |
| | 3 | 100.5 | — | 0.440 | 99.96 |
| | 4 | 100.7 | — | 0.440 | 99.76 |
| | 6 | 104.0 | — | 0.455 | 99.88 |
| | 7 | 103.2 | — | 0.450 | 99.60 |
| | 8 | 101.0 | — | 0.435 | 99.33 |
| | 9 | 95.6 | — | 0.412 | 98.25 |

The data shown in Table 7 were worked out according to the Rogers' method, drawing up the values of the energies of activation of the decomposition reactions under dry and wet conditions, the specific rate constants as well as the validity period. The related results are shown in Table 8.

TABLE 8

Energies of activation, specific velocities and periods of validity

| Substance | Conditions | Activ. en. as Kcal/mole | K at 25° in hours$^{-1}$ | Validity period |
|---|---|---|---|---|
| 2-thiopropionyl-glycine | dry | 15.66 | $2.58 \cdot 10^{-6}$ | 40847 hours = 1702 days ≈ 4 years 8 months |
| | wet | 11.54 | $2.14 \cdot 10^{-5}$ | 4924 hours = 205 days |
| 2-(2-thenoyl thio)-propionyl glycine | dry | 12.28 | 0 | unlimited |
| | wet | 13.27 | $2.61 \cdot 10^{-6}$ | 40377 hours = 1682 days ≈ 4 years 7 months |

The markedly better stability of 2-(2-thenoylthio)-propionyl-glycine (I) results evident also from the data of Table 8. For a therapeutic use as a liyer-protective agent, the compound (I) can be formulated as capsules of 100–400 mg as well as of syrups containing such dosate-strengths as to provide correspondent unit doses.

The daily dosage schedule is 2–4 capsules of 250 mg, 1 or more ampuls of 250 mg to be given intramuscularly or intravenously as well as 2–3 tablespoonfuls of syrup for an approximate dosage strength of 250 mg in each tablespoonful.

MUCOLYTIC AND BRONCHIAL-SPASM RELIEVING ACTIVITY (a) Experimental Bronchitis in the Rat The mucolytic activity of (I) was assessed in the rat subjected to a bronchopulmonary impairment induced by a $SO_2$ inhalation.

For the purpose 40 male rats, Sprague-Dawley strain, 320–370 grams, subdivided into 4 groups each consisting of 10 elements were subjected to the following treatments:

Group 1: poisoning treatment ($SO_2$)

Group 2: poisoning with $SO_2$, and aerosol treatment with (I).

Group 3: poisoning with $SO_2$, and aerosol treatment with (I).

Group 4: poisoning with $SO_2$, and subcutaneous treatment with (I).

In any case the dose of (I) was 50 mg/kg.

For the poisoning-induction the animals were subjected to a constant air flow containing $SO_2$ at a 0.03 percent concentration. The poisoning treatment was given for 15 days subjecting the rats, 2 hours daily, to an inhalation of $SO_2$ for 15-minute periods. Concurrently the protective treatment with (I) was carried out in the groups in which it had been scheduled. The animals were killed on the day following the last inhalation.

The lungs were withdrawn together with the trachea, fixed in 10 percent formalin, and subjected to a macroscopic examination, dipped thereafter into the same fixing fluid for 24 hours, and thereafter for one hour in absolute ethanol.

The bronchial tree was thereafter evidenced with alcian blue; moreover, a subsequent staining was made with the Schiff's reagent in order to evidence the muchopolysaccharides.

Each lung was given the following arbitary score:

(1) Macroscopic Examination:

0 = normal lung;
1 = reddened lung;
2 = few hemorrhagic spots
3 = many hemorrhagic spots
4 = some hemorrhagic spots
5 = large hemorrhagic spots

(2) Visualization of the Bronchial Tree with Alcian Blue:

0 = uniform staining
1 = almost uniform staining
2 = irregular staining
3 = quite irregular staining.

(3) Bronchopulmonary Alterations at the Microscopic Examination:

0 = no alterations
1 = mild alterations
2 = fair alterations
3 = relevant alterations The results are reported in the following tables.

TABLE 9

| | Macroscopic Examination | | | |
|---|---|---|---|---|
| | GROUPS | | | |
| | 1 | 2 | 3 | 4 |
| E | 4.00 ± 0.26 | 1.25 ± 0.31 | 1.12 ± 0.39 | 1.25 ± 0.36 |
| S | — | h.s. | h.s. | h.s. |

E = evaluation; mean ± standard error
S = significance vs. controls
h.s. = highly significant

TABLE 10

| | Visualization of the bronchial tract | | | |
|---|---|---|---|---|
| | GROUPS | | | |
| | 1 | 2 | 3 | 4 |
| E | 2.50 ± 0.26 | 0.87 ± 0.29 | 0.87 ± 0.29 | 0.75 ± 0.31 |
| S | — | h.s. | h.s. | h.s. |

NOTE:
See TABLE 9 for explanation of symbols

TABLE 11

| | Microscopic Examination | | | |
|---|---|---|---|---|
| | GROUPS | | | |
| | 1 | 2 | 3 | 4 |
| E | 2.75 ± 0.16 | 0.87 ± 0.29 | 0.75 ± 0.31 | 1.00 ± 0.26 |
| S | — | h.s. | h.s. | h.s. |

NOTE:
See TABLE 9 for explanation of symbols

Both the results obtained and their high significance enable to state that the compound (I) exerts a marked protective action with respect to the experimental bronchitis induced in the rat by an inhalation of $SO_2$.

(b) Experimental Bronchitis due to Citric Acid in the Guinea-Pig

Twenty-four spotted guinea-pigs, Morini strain, bodyweight 450 grams approximately, were used for the investigation, subdivided into 4 groups, each consisting of 6 animals, subjected to the following treatments:

Group 1: poisoning treatment with citric acid
Group 2: treatment with citric acid, and thereafter with (I) orally.
Group 3: treatment with citric acid, and thereafter with (I) by aerosol administration.
Group 4: treatment with citric acid, and thereafter with (I) rectally.

In any case the dose of (I) was 50 mg/kg.

The poisoning was made introducing the experimental animals into tight-sealed plexiglass cages containing a solution of 7.5 percent citric acid for 15 minutes daily, 6 days weekly, for 4 weeks. Concurrently to the poisoning treatment, the treatment with (I) was given in all those cases in which the treatment with (I) had been scheduled.

The animals were sacrificed on the day after the last application, and the lungs were subjected to the same treatments and to the same assessments performed with the same scores already used in the case of the rat.

The related results are reported in the following Tables.

TABLE 12

| | MICROSCOPIC EXAMINATION | | | |
|---|---|---|---|---|
| | GROUPS | | | |
| | 1 | 2 | 3 | 4 |
| E | 4.00 ± 0.25 | 2.00 ± 0.36 | 2.33 ± 0.49 | 1.83 ± 0.40 |
| S | — | h.s. | h.s. | h.s. |

NOTE:
See TABLE 9 for explanation symbols

TABLE 13

| | VISUALIZATION OF THE BRONCHIAL TRACT | | | |
|---|---|---|---|---|
| | GROUPS | | | |
| | 1 | 2 | 3 | 4 |
| E | 2.83 ± 0.16 | 1.16 ± 0.30 | 1.00 ± 0.36 | 1.00 ± 0.44 |
| S | — | h.s. | h.s. | h.s. |

NOTE:
See TABLE 9 for explanation of symbols

TABLE 14

| | MICROSCOPIC EXAMINATION | | | |
|---|---|---|---|---|
| | GROUPS | | | |
| | 1 | 2 | 3 | 4 |
| E | 3.00 ± 0.00 | 0.83 ± 0.30 | 1.00 ± 0.36 | 0.66 ± 0.42 |
| S | — | h.s. | h.s. | h.s. |

NOTE:
See TABLE 9 for explanation of symbols

The results obtained enable to state that (I) exerts a marked protective action in the case of an experimental bronchitis induced in the guinea-pig by an inhalation of citric acid.

(c) Bronchial Spasm due to Histamine Aeresol in the Guinea-Pig

Thirty spotted guinea-pigs, male, Morini strain, 400–500 g bodyweight, were used for the investigation, subdivided into 5 lots, each consisting of 6 animals. The animals were singly placed in a tightly sealed plexiglas cage into which a 0.1 percent aqueous solution of histamine hydrochloride was aerosolized. The time of resistance to the spasm was calculated from the moment of introduction into the cage up to the time of the appearance of the dyspnea crisis. The results were repeated after 24 hours and after one hour from the following treatments:

Group 1: controls with no treatment
Group 2: treated with (I) given orally
Group 3: treated with (I) given by aerosol administration
Group 4: treated with (I) intraperitoneally
Group 5: treated with (I) rectally.

In any case, the dose was 50 mg/kg.

The results obtained are reported in the following tables.

TABLE 15

Bronchial-spasm relieving activity of (I).
Detections before the treatment.

| | GROUPS | | | |
|---|---|---|---|---|
| 1 | 2 | 3 | 4 | 5 |
| E 116.8 ± 4.73 | 116.00 ± 8.84 | 113.00 ± 5.62 | 112.16 ± 7.9 | 117.5 ± 6.39 |

E = Evaluation; mean ± standard error, expressed in seconds. The groups are statistically homogeneous.

TABLE 16

Bronchial-spasm relieving activity of (I).
Detections one hour after the treatment.

| | 1 | 2 | 3 | 4 | 5 |
|---|---|---|---|---|---|
| E | 114.1 ± 5.4 | 184.7 ± 14.2 | 170.3 ± 10.9 | 187.2 ± 16.1 | 178.5 ± 11.9 |
| S | — | h.s. | h.s. | h.s. | h.s. |

Note:
See TABLE 9 for explanation of symbols.

The results obtained enable to state that the compound (I) exerts a remarkable bronchial-spasm relieving action by all the assessed routes of administration.

The results of the pharmacological investigation, associated with the very low toxicity of the compound (I), enabled directly to start clinical trials in man.

The results obtained can be summarized in the following terms.

(d) Clinical Trials

The drug was assessed, with respect to its mucolytic action, on thirty elderly patients (mean age 57 years, maximal 87, mean age 72). Twenty-six of them developed a marked improvement with respect to the starting clinical conditions after receiving daily, for six consecutive days, two suppositories daily, each containing 0.36 grams of the compound (I). The improvement was assessed on the basis of the following parameters:

decrease of the daily quantity of sputum;
decrease of the viscosity of the sputum;
increase of the Tiffeneau's index;
improved value of the erythrocyte sedimentation rate.

A group of twenty patients, in the same mean age, was given for control purposes a known drug such as N-acetylcysteine. Although the results obtained with N-acetylcysteine are overall comparable with those provided by the compound (I) with respect to the decrease of the sputum, it was observed that the compound (I) proves markedly better in terms of rapidity of action.

The superiority of (I) over N-acetylcysteine is moreover provided by the administration in the form of aerosol: actually, no fit of cough was observed in the case of (I) as, on the contrary, frequently happens in the case of patients subjected to an aerosol administration with N-acetylcysteine.

(e) Clinical Trials (in Pediatry)

In the course of a clinical trial aimed at assessing the mucolytic efficacy of the compound (I) in bronchopneumopathies of the pediatric age, fifty patients, ranging in age from 3 months to 9 years (mean age, 26 months) were treated for the presence of an acute infectious inflammatory condition of the respiratory tract characterized by a bronchial hypersecretion or, in some cases, by a mucoviscidosis syndrome.

The results proved markedly positive for 45 patients (90 percent) with normalization of the following parameters:

cough
dyspnea
wet sounds on auscultation.

Moreover a mean decrease of the viscosimetric value of the mucus was evidenced, ie from 292.4±92.1 g/Hg to 155.4±61.3 g/Hg.

(f) Pharmaceutical Formulations Ampuls for Aerosol Administration or Intramuscular Administration Each ampul contains:

| | |
|---|---|
| 2-(2-thenoylthio)-propionylglycine sodium salt | 0.360 g |
| sodium metabisulfite | 10 mg |
| pyrogen-free, distilled water | 3 ml |
| Syrup | |
| 2-(2-thenoylthio)-propionylglycine sodium salt | 3.60 g |
| sorbitol, 70 percent | 15 g |
| sucrose | 50 g |
| ethanol | 1 ml |
| p-hydroxybenzoates | 0.5 ml |
| flavoring agents | 0.5 ml |
| distilled water | qs to 100 ml |
| saccharin | 0.20 g |
| Suppositories for Adults | |
| 2-(2-thenoylthio)-propionylglycine sodium salt | 0.360 g |
| sodium metabisulfite | 0.020 g |
| excipients q.s. to I suppository | |
| Pediatric Suppositories | |
| 2-(2-thenoylthio)-propionylglycine sodium salt | 0.180 g |
| Sodium metabisulfite | 0.005 g |
| Excipient qs to I suppository | |
| Single - Dose Sacks (5 g) | |
| Each 100 grams contains: | |
| 2-(2-thenoylthio)-propionylglycine sodium salt | 3.60 g |

| -continued | |
|---|---|
| saccharin | 0.20 g |
| orange flavour | 0.5 g |
| orange lyophilyzate | 10 g |
| sucrose to | 100 g |

I claim:

1. 2-(2-thenoylthio)-propionylglycine as a new compound, characterized by the structural formula (I)

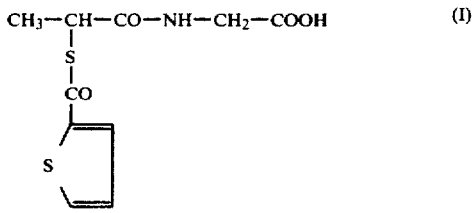

2. Pharmaceutical composition for the treatment of acute and chronic liver diseases as well as poisoning consequences, characterized by the fact that 2-(2-thenoylthio)-propionylglycine, with the structural formula (I), and/or one of its pharmacologically acceptable salt, is contained as the active ingredient.

3. Pharmaceutical composition, endowed with a mucolytic and bronchial-spasm relieving activity, characterized by the fact that 2-(2-thenoylthio)-propionylglycine, with the structural formula (I), and/or one of its pharmacologically acceptable salts, is contained as the active ingredient.

4. Pharmaceutical composition, according to claim 2, characterized by the fact that the sodium salt of 2-(2-thenoylthio)-propionylglycine (I) is contained as the active ingredient.

5. Pharmaceutical composition, according to claim 2, available in the pharmaceutical dosage form of tablets, suppositories, injectable ampuls, syrup or aerosol.